(12) United States Patent
Romanski et al.

(10) Patent No.: US 12,077,455 B2
(45) Date of Patent: Sep. 3, 2024

(54) RECEPTOR AND METHOD FOR REMOVING OXOANIONS FROM AQUEOUS PHASE

(71) Applicant: UNIWERSYTET WARSZAWSKI, Warsaw (PL)

(72) Inventors: Jan Romanski, Stroze (PL); Damian Jagleniec, Koden (PL); Marcin Karbarz, Warsaw (PL)

(73) Assignee: UNIWERSYTET WARSZAWSKI, Warsaw (PL)

( * ) Notice: Subject to any disclaimer, the term of this patent is extended or adjusted under 35 U.S.C. 154(b) by 456 days.

(21) Appl. No.: 17/436,780

(22) PCT Filed: Mar. 6, 2020

(86) PCT No.: PCT/PL2020/000025
§ 371 (c)(1),
(2) Date: Sep. 7, 2021

(87) PCT Pub. No.: WO2020/180199
PCT Pub. Date: Sep. 10, 2020

(65) Prior Publication Data
US 2022/0169536 A1    Jun. 2, 2022

(30) Foreign Application Priority Data
Mar. 6, 2019 (PL) .......................... 429164

(51) Int. Cl.
*C02F 1/28* (2023.01)
*C02F 1/68* (2023.01)
(Continued)

(52) U.S. Cl.
CPC ............. *C02F 1/285* (2013.01); *C02F 1/683* (2013.01); *C07D 323/00* (2013.01); *G01N 21/78* (2013.01);
(Continued)

(58) Field of Classification Search
CPC ......... C02F 1/285; C02F 1/683; C07D 323/00
See application file for complete search history.

(56) References Cited

U.S. PATENT DOCUMENTS 9,260,326 B2    2/2016   Custelcean et al.

OTHER PUBLICATIONS

Qin, Lei, et al. "Macrocyclic squaramides: anion receptors with high sulfate binding affinity and selectivity in aqueous media." Chemical Science 7.7 (2016): 4563-4572. (Year: 2016).*

(Continued)

*Primary Examiner* — Bradley R Spies
(74) *Attorney, Agent, or Firm* — Dickinson Wright PLLC; Andrew D. Dorisio

(57) ABSTRACT

A receptor for the simultaneous removal of oxoanions and their counterions from aqueous phase, particularly containing radioactive wastes, containing amide groups specifically coordinating the oxoanions, as well as moieties specifically coordinating cations, according to the present invention is characterised in that it contains within one molecule domains binding oxoanions and domains binding cations, preferably adapting a molecular structure of a general formula: (I) wherein Z this is a group containing crown ether, preferably a benzocrown group, X is any substituent, including the Y—Z grouping, and Y is any substituent or 0 (i.e. a direct bond between N and Z), where the oxoanion binding domain is a squaramide unit coordinating the oxoanions through amide groups, and squaramide contains additional substituents that increase or decrease the acidity of its amide protons, compared to unsubstituted squaramide, whereas the counter ion binding domain is a crown ether of a size adjusted to the type of binding cation, which forms part of at least one of the aforementioned substituents of squaramide, where the receptor has the ability to remove oxoanions and their counterions from aqueous phase to another (Continued)

water-immiscible phase, preferably to organic phase, and has the ability to form soluble complexes in at least one of the aforementioned phases. The invention considers also a method of removing oxoanions in the form of inorganic salts from aqueous phase, using receptors of the invention in the form of organic molecules containing amide groups, according to the invention is characterised in that it uses the aforementioned receptors for simultaneous binding of oxoanions and their counterions in aqueous phase, preferably acidic when using the receptor with substituents increasing acidity of squaramide protons, or alkaline when using the receptor with substituents decreasing acidity of squaramide protons. A sensor for detecting oxoanions according to the invention is characterised in that it uses the aforementioned receptors, dissolved or suspended in an organic solvent or in a mixture of organic solvents, forming coloured complexes in contact with the phase containing given oxoanions. The preparation for removing oxoanions from aqueous solutions, particularly containing radioactive waste at the stage preceding their disposal by vitrification, is characterised in that it contains the receptor according to the invention, dissolved or suspended in the water-immiscible phase, and the appropriate amount of counterion facilitating extraction. A process of utilisation of aqueous solutions by vitrification, particularly solutions containing radioactive waste, is characterised in that vitrification step is preceded by the step of oxoanions removal, preferably sulfate(VI) anions, by the method according to the invention, using the receptors according to the invention, preferably using the preparation according to the invention.

16 Claims, 7 Drawing Sheets

(51) Int. Cl.
  C07D 323/00  (2006.01)
  G01N 21/78  (2006.01)
  G21F 9/12  (2006.01)
  G21F 9/16  (2006.01)
  C02F 101/00  (2006.01)
  C02F 101/10  (2006.01)
  C02F 101/16  (2006.01)

(52) U.S. Cl.
  CPC ............... *G21F 9/12* (2013.01); *G21F 9/162* (2013.01); *C02F 2101/006* (2013.01); *C02F 2101/101* (2013.01); *C02F 2101/163* (2013.01)

(56) References Cited

OTHER PUBLICATIONS

Damian Jagleniec et al. "Recognition and Extraction of Sodium Chloride by a Squaramide-Based Ion Pair Receptor", Inorganic Chemistry, vol. 57, No. 20, (Oct. 1, 2018). pp. 12941-12952, XP055710798, Easton, US.

Szymon Zdanowski et al. "An ion pair receptor facilitating the extraction of chloride salt from the aqueous to the organic phase", New Journal of Chemistry, vol. 40, No. 8, (Jan. 1, 2016), pp. 7190-7196, XP055710804, GB.

Dominika Zalubiniak et al. "Highly effective ion-pair receptors based on 2, 2-bis (aminomethyl)—propionic acid", Dalton Transactions, vol. 45, No. 39, (Jan. 1, 2016), pp. 15557-15564, XP055710799, ISSN: 1477-9226, DOI: 10.1039/C6DT02833K figures 1-4 p. 15558, col. 2, line 1-p. 15561, col. 2, line 23.

Antonio Frontera et al. "Preparation, Solid-State Characterization, and Computational Study of a Crown Ether Attached to a Squarmide", Organic Letters, vol. 7, No. 8, (Apr. 1, 2005), pp. 1437-1440, XP055710800, US.

Fowler, et al. "Enhanced Anion Exchange for Selective Sulfate Extraction"; Chemical Sciences Division, Oak Ridge National Laboratory; Tennessee, Aug. 16, 2008.

Jia, et al.; "Highly Efficient Extraction of Sulfate Ions eith a Tripodal Hexaurea"; Agnew Chem. Int. Ed. 201; www.angewandte.org.

Ziach, et al.; "Cooperative binding and extraction of sodium nitrite by a ditopic receptor incorporated into a polymeric resin"; Royal Society of Chemistry; Jun. 3, 2016.

Ziach, et al.; "Sodium thiocyanate binding by a 3-aminobenzoic acid based ion pair receptor consisting of a thiourea binding domain"; Inorganic Chemistry Communications; May 30, 2017; Poland.

Pflugrath, et al.; "Sulphate sequestered in sulphate-binding protein of *Salmonella typhimurium* is bound solely by hydrogen bonds" Department of Biochemistry; Rice University; Houston, Texas; 1985.

* cited by examiner

RECEPTOR AND METHOD FOR REMOVING OXOANIONS FROM AQUEOUS PHASE

TECHNICAL FIELD

The subject of the invention is a receptor for the simultaneous removal of oxoanions and their inorganic counterions from the aqueous phase, as well as a method for the removal of oxoanions from the aqueous phase, a sensor for the detection of oxoanions, a preparation for the removal of oxoanions from the aqueous phase and an improved process of utilization of aqueous solutions by vitrification. The receptor binds oxoanions with amide groups.

BACKGROUND

Cleaning aqueous solutions of various types of pollution is extremely important in the modern economy. The issue of selective oxoanion removal from aqueous solutions is difficult to solve due to their good water solubility and often similar chemical properties. It is particularly difficult to purify aqueous solutions from oxoanions exhibiting hydrophilic properties (e.g. sulfates (VI), hydration energy—1090 kJ/mol), because they have a small tendency to form poorly soluble salts that could be precipitated, and also they have no affinity for organic solvents, which makes them difficult to extract. It is much easier to clean aqueous solutions of salts containing lipophilic anions (e.g. nitrates (V), hydration energy—306 kJ/mol).

Particularly important is the problem of sulfate(VI) anions removal from HLLW (high level liquid waste) radioactive waste at the stage of their utilisation. Effective removal of sulfate(VI) anions form radioactive waste is crucial for the proper vitrification of waste, because sulfates(VI) have low solubility in borosilicate glass. In the presence of excess of sulfates(VI), borosilicate glass corrodes and breaks, which leads to hazardous radioactive leaks. Removal of sulfates (VI) is problematic because using all conventional methods of oxoanion removal, because sulfate(VI) anions are normally being removed as one of the last species following the Hofmeister series. Therefore, removal of sulfate(VI) anions needs preliminary purification of the solution from all anions standing before sulfates(VI) in Hofmeister series, e.g. nitrates(V), which makes the process burdensome, long-lasting and expensive.

Proteins capable of binding sulfate(VI) anions are known [J. W. Pflugrath et al., *Nature,* 314 (1985) 257]. These proteins (sulfate binding proteins) contain moieties that coordinate oxygen atoms in sulfate(VI) anions. Unfortunately, there are no reports so far describing the possibility of using these proteins as receptors for the extraction of sulfates(VI) from aqueous solutions.

A method for removing oxoanions from aqueous phase towards organic phase (liquid-liquid extraction) is known. It requires using anion receptor and bulky, lipophilic counterion (e.g. tertaalkylammonium, tetrafenylborate) [C. Jia et al., *Angew. Chem. Int. Ed.* 50 (2011) 486; C. J. Fowler et al., *J. Am. Chem. Soc.* 130 (2008) 14386]. This method allows to transfer hydrophilic oxoanions to another liquid phase, but due to the need to using both the receptor and the bulky counterion, it is burdensome, expensive and difficult to use on an industrial scale.

Neutral anion receptors capable for selective removal of oxoanions from aqueous solutions are known [R. Culcestean et al., U.S. Pat. No. 9,260,326 B2]. These receptors are in the form of tripodal ligands containing urea groups. These ligands, when dissolved in an aqueous solution containing oxoanions, especially sulfates(VI) and chromates(IV), bind these oxoanions forming a shell around them, and then precipitate together with counterions such as $Na^+$ and $K^+$ cations, forming a precipitate. The process of precipitation of complexes containing oxoanions takes place in an alkaline environment (pH in the range of 9.5-14.0), at room temperature, lasts four days and requires constant stirring. Ligands can then be recovered following a dedicated 24 hours procedure. This method allows the separation of oxoanions from the aqueous phase with an efficiency above 90%, however, it is time consuming and multi-stage, which reduces the possibility of its industrial use.

Neutral ion pair receptors able to bind cations and anions simultaneously are known [K. Ziach et al., *Dalton Trans.* 45 (2016) 11639; K. Ziach et al., *Inorg. Chem. Commun.* 84 (2017) 251]. These receptors contain binding domains with urea or thiourea groups to bind anions, as well as binding domains with crown ethers to bind alkaline metal cations. These receptors are capable of coordinating salt also in an immobilised form on a heterogeneous medium. However, such receptors are not effective for removing oxoanions from the aqueous phase, most likely due to the inefficient way of arrangement of binding domains as well as their too low binding force.

Neutral, amino acid based, ion pair receptors capable of simultaneously binding cations and anions are known. Such receptors contain a squaramide moiety as an anion binding domain and crown ether moiety as counterion bind domain [S. Zdanowski et al., *New J. Chem.* 40 (2016) 7190]. These receptors are capable of coordinating ion pairs in acetonitrile. They are also capable of extracting chloride salts associated with bulky, lipophilic cation from aqueous to organic phase. Nevertheless, this kind of receptors are not effective for removing oxoanions form aqueous phase, most likely due to insufficient binding force of the receptor, which is unable to coordinate two strongly hydrated ions in the organic phase due to preferential coordination of anions and formation of an ion pair with strongly interacting cations (e.g. sodium) outside the receptor molecule.

Neutral ion pair receptors able to simultaneously bind cations and anions, containing a squaramide moiety for binding anions, and a benzo-15-crown-5 ether for binding alkali metal cations are known [D. Jaglaniec et al., *Inorg, Chem.* 57 (2018) 12941]. These receptors are designed to remove, for example, sodium chloride from the aqueous phase to nitrobenzene by extraction. The formed complexes are not soluble in the organic phase at concentrations higher than approximately 1 mM, which impedes their effective extraction from aqueous phase due to precipitation of the complex at the interface. This is particularly unfavourable when trying to use these receptors industrially to remove ion pairs from aqueous solutions. Because of the lack of selectivity, these neutral ion pair receptors also are not suitable for separation or selective removal of specific ions.

There is a high unmet demand to design receptors for removal of oxoanions and their counterions, especially those exhibiting high hydration energy, from aqueous phase, which receptors, after coordinating these ionic pairs, would remain dissolved in the organic phase at significantly high concentrations, allowing quick and easy extraction of said oxoanions and their counter ions from aqueous phase. This high unmet demand is particularly problematic upon treatment of radioactive waste to clean them from sulfate(VI) anions at the stage preceding the process of vitrification of this waste, because the presence of traces of sulfates(VI) in the sample makes it impossible to create a durable and tight borosilicate glass logs. The problem of removing oxoanions from aqueous phase is also significant in the context of hard water treatment, in order to prevent scale formation in industrial and civil installations.

SUMMARY

A receptor for the simultaneous removal of oxoanions and their counterions from aqueous phase, containing amide groups specifically coordinating the oxoanions, as well as moieties specifically coordinating cations, according to the invention is characterised in that it contains within one molecule domains binding oxoanions and domains binding cations, preferably adapting a molecular structure of a general formula:

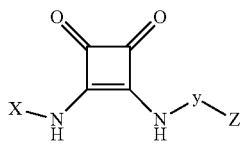

wherein Z this is a group containing crown ether, preferably a benzocrown group, X is any substituent, including the Y—Z grouping, and Y is any substituent or Ø (i.e. a direct bond between N and Z), where the oxoanion binding domain is a squaramide unit coordinating the oxoanions through amide groups, and squaramide contains additional substituents that increase the acidity of its amide protons, compared to unsubstituted squaramide, whereas the counter ion binding domain is a crown ether of a size adjusted to the type of binding cation, which forms part of at least one of the aforementioned substituents of squaramide, where the receptor has the ability to remove oxoanions and their counterions from aqueous phase to another water-immiscible phase, preferably to organic phase, and has the ability to form soluble complexes in at least one of the aforementioned phases.

In the receptor according to the invention, crown ether is connected to squaramide unit through an aromatic ring. Benzocrown moiety is connected to squaramide via a linker in the form of alkyl chain, preferably containing moieties capable of creating hydrogen bonds, e.g. amide, thioamide, urea, thiourea or ester. Crown ether is 12-crown-4-ether, 15-crown-5-ether, 18-crown-6, 21-crown-7 ether or their analogues containing heteroatoms, preferably with additional substitutes or without additional substitutes. Preferably, crown ether or benzo-crown ether is a part of each of the two substitutes of squaramide.

In the receptor according to the invention, squaramide substituent is an aromatic ring with substituents reducing its electron density, preferably with substituents such as: —F, —$CF_3$ or —$NO_2$.

Squaramide substituent is an aromatic ring with substituents having positive charge, preferably with substituents such as: —$N^+(Alkyl)_3$ or —$N^+(Phenyl)_3$. Squaramide substituent is tris(2-aminoethyl)amine. Tris(2-aminoethyl) amine is a linking group between two or three squaramides connected to counterion binding domains, preferably crown ether or benzo-crown ether. The substituents are in any position of the aromatic ring, in several positions simultaneously and in any combination. Oxoanions bound by receptor are monovalent oxoanions, preferably nitrite or nitrate(V), bivalent oxoanions, preferably sulfite, sulfate (VI), rhenate(VII), technetate(VII), or trivalent oxoanions, preferably phosphate(V). Counterions are inorganic cations, preferably metal cations of group 1 or group 2 of the periodic table and radioactive cations, or lanthanide and actinide cations, preferably $Li^+$, $Na^+$, $K^+$, $Cs^+$. Preferably counterions are also ammonium cations, $NH_{4+}$, $N^+(Alkyl)_4$, $N^+(Phenyl)_4$ or tetraphenylborate cations. Particularly important is aqueous phase containing oxoanions and their counetrions, containing radioactive compounds.

The receptor according to the invention, can be regenerated by washing with water, preferably with clean water, preferably with distilled water or deionized water.

A method of removing oxoanions in the form of inorganic salts from aqueous phase, using receptors in the form of organic molecules containing amide groups, according to the invention is characterised in that it uses the aforementioned receptors for simultaneous binding of oxoanions and their counterions in aqueous phase, preferably acidic when using the receptor with substituents increasing acidity of squaramide protons, or alkaline when using the receptor with substituents decreasing acidity of squaramide protons.

According to the method of the invention, oxoanions and their counterions are being removed from aqueous phase to organic phase by dissolving or suspending the receptor in a suitably selected organic solvent or in a mixture of organic solvents, and then extraction of the given oxoanions and their counterions from the aqueous phase to this organic phase, where the oxoanions and their counterions are simultaneously bound by the receptor in the form of a soluble complex. Alternatively, oxoanions and their counterions are removed from aqueous phase to organic phase by dissolving or suspending the receptor in aqueous phase containing the given oxoanions and their counterions, simultaneous binding of oxoanions and their counterions by the receptor, followed by extraction of the formed complex containing oxoanion and its counterions complex to a suitably selected organic solvent or a mixture of organic solvents in the form of a soluble complex. The organic solvent or mixture of organic solvents preferably contains chloroform. According to the invention, oxoanions and their inorganic counterions are being removed from the aqueous phase to solid phase by passing the aqueous phase containing the given oxoanions and their counterions, through a stationary phase containing an immobilised receptor. Oxoanions and their counterions are being removed from aqueous phase to solid phase with use of a homogeneous or heterogeneous medium with an immobilised receptor, preferably in the form of a polymer, crosslinked polymer, nanoparticles, magnetic nanoparticles, porous materials. According to the invention, oxoanions and their counterions are being removed from one aqueous phase to another aqueous or organic phase by using a membrane in a form of a layer of organic solution containing a dissolved receptor or in a solid form with an immobilized receptor, separating these aqueous phases. Preferably, by the method according to the invention, sulfate(VI) oxoanions are being removed from aqueous solutions in the presence of at least a stoichiometric amount of potassium cations as counterions, using a receptor of the formula shown below or its derivatives:

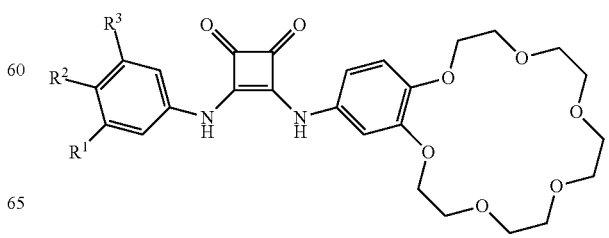

-continued

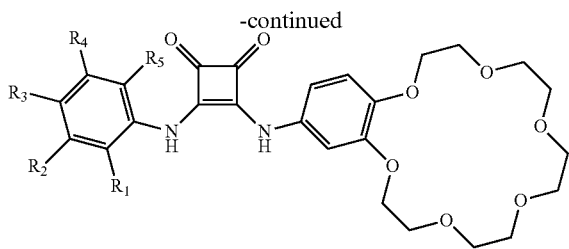

wherein $R^1$, $R^2$, $R^3$, $R^4$ and $R^5$ are hydrogens, or the same or different substituents reducing the electron density of the aromatic ring, preferably —F, —$CF_3$ or —$NO_2$.

A sensor for detecting oxoanions according to the invention is characterised in that it uses the aforementioned receptors, immobilised on a heterogeneous substrate, or dissolved or suspended in an organic solvent or in a mixture of organic solvents, forming coloured complexes in contact with the phase containing given oxoanions.

The preparation for removing oxoanions from aqueous solutions, particularly containing radioactive waste at the stage preceding their disposal by vitrification, according to the invention is characterised in that it contains the aforementioned receptor, dissolved or suspended in the water-immiscible phase, and the appropriate amount of counterion facilitating extraction. The preparation for the removal of sulfate(VI) anions contains a receptor of a structural formula described above or its derivatives, as well as potassium cations at least twice lower concentration and lipophilic anions equilibrating their charge, preferably e.g. perchlorates, hexafluorophosphates, tetrafluoroborates.

A process of utilisation of aqueous solutions by vitrification, particularly solutions containing radioactive waste, according to the invention is characterised in that vitrification step is preceded by the step of oxoanions removal, preferably sulfate(VI) anions, by the aforementioned method, using the aforementioned receptors, preferably using the aforementioned preparation.

BRIEF DESCRIPTION OF THE DRAWINGS

The receptor for removing oxoanions from the aqueous phase, the method of removing oxoanions in the form of inorganic salts from aqueous phase, and the sensor for detecting oxoanions are described in detail below, with reference to the attached drawing, in which.

Figure 7:
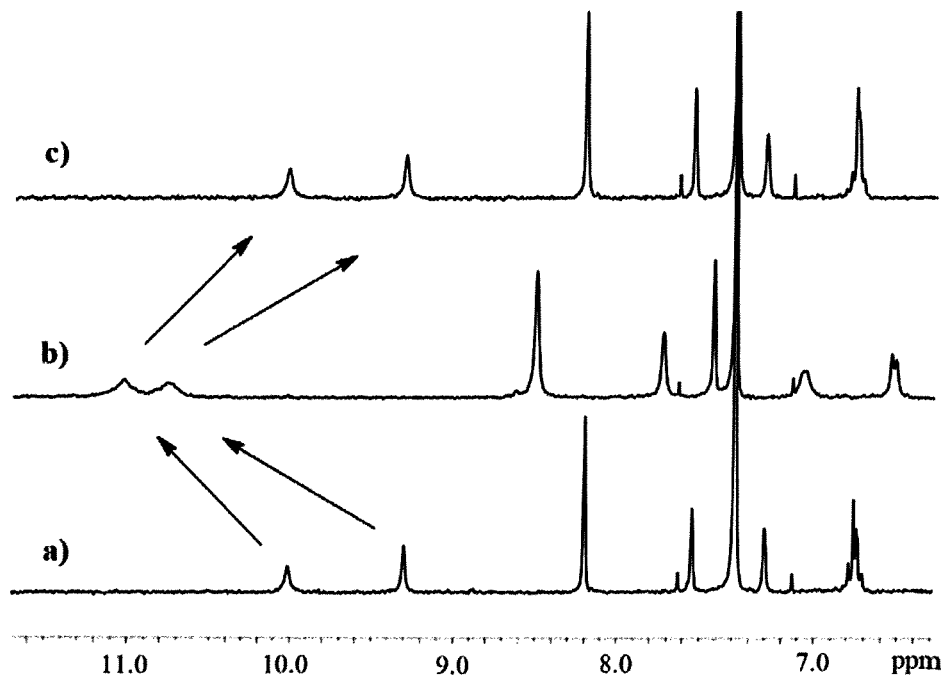
Figure 8:
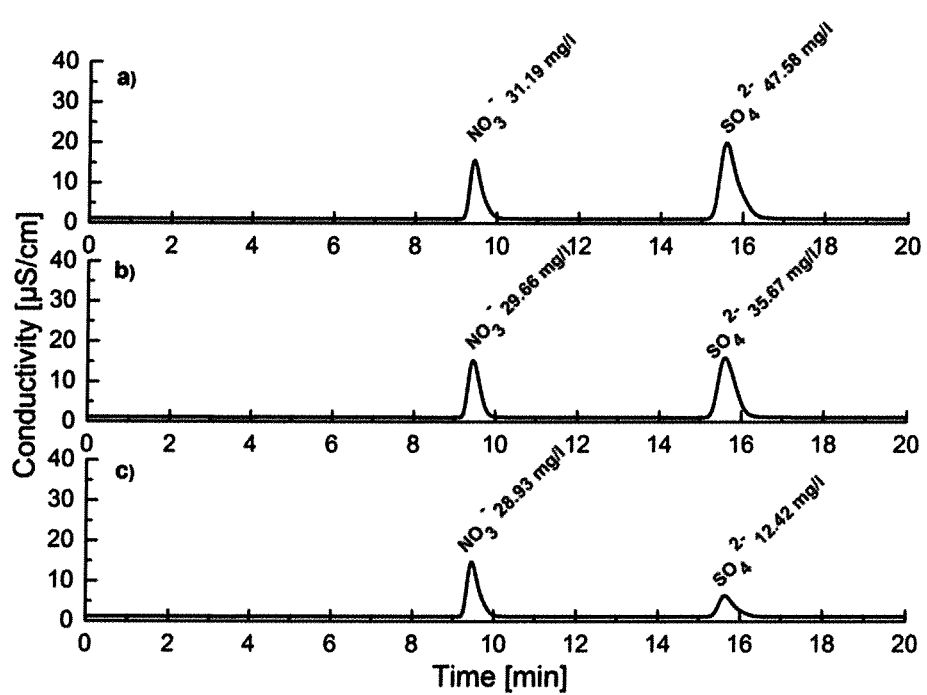

R1—receptor solution/suspension (the phase immiscible with aqueous solution),
O1—waste containing oxoanion (sulfate), preferably an aqueous solution,
R2—solution containing a receptor complex with oxoanion (sulfate),
O2—waste with reduced content of oxoanions (sulfate),
W—an aqueous phase, preferably pure, deionized water;

FIG. 7 shows $^1$HNMR spectra obtained in Example 2: a) receptor in chloroform after contacting with the aqueous phase, b) receptor binding $K_2SO_4$, c) receptor regenerated with use of distilled water;

FIG. 8 shows the chromatographically determined changes in the concentration of nitrates(V) and sulfates(VI) in the solution subjected to extraction with use of the receptor solution in $CHCl_3$ according to Example 4.

Figure 9:
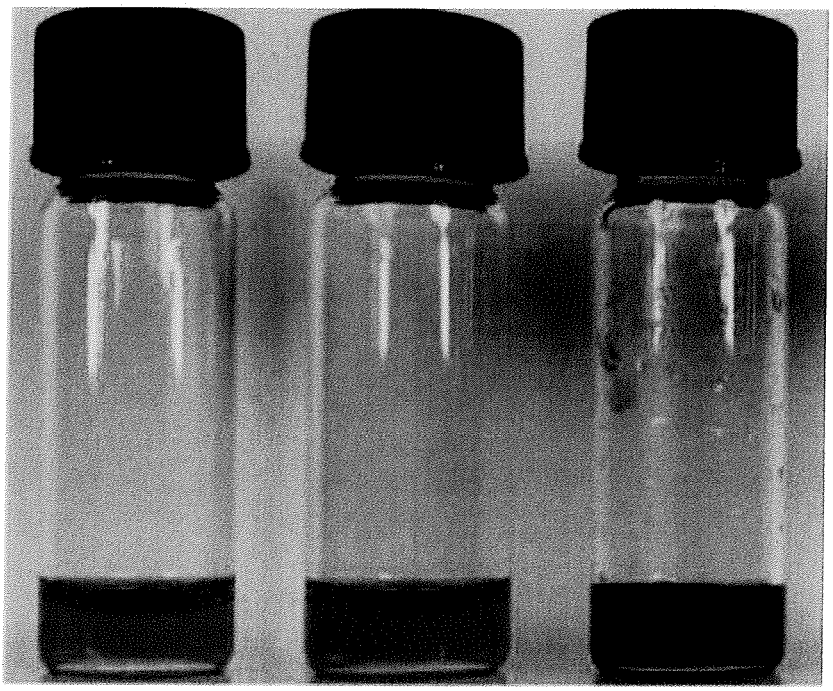
Figure 10:
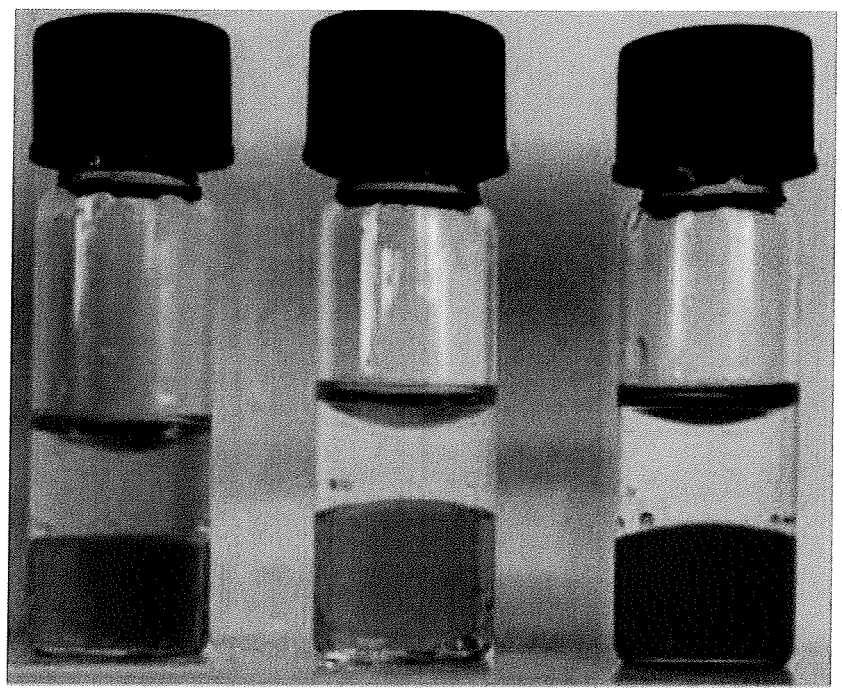
Figure 11:
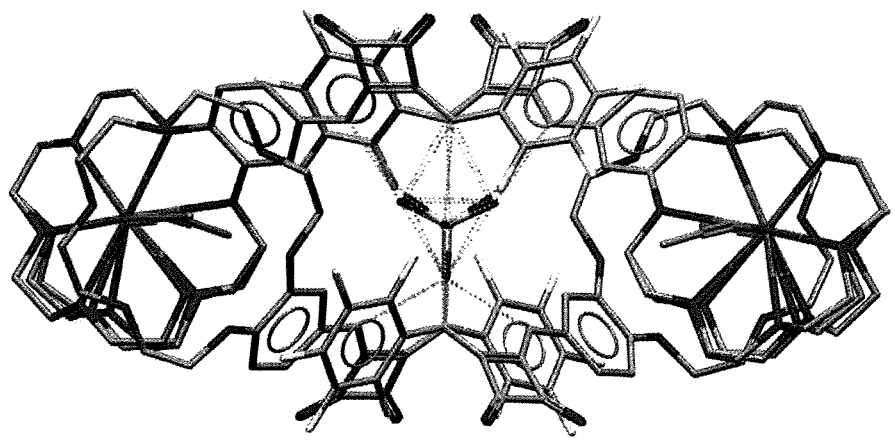
Figure 12:
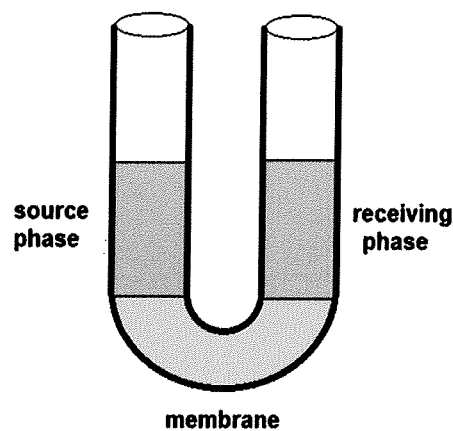
Figure 13:
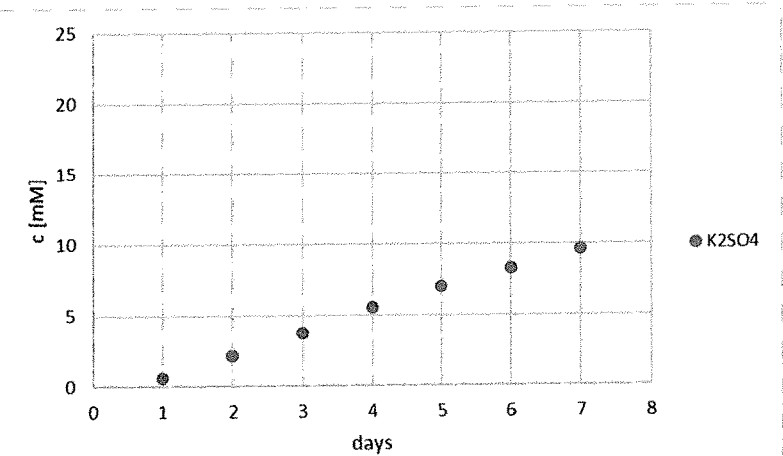
Figure 14:
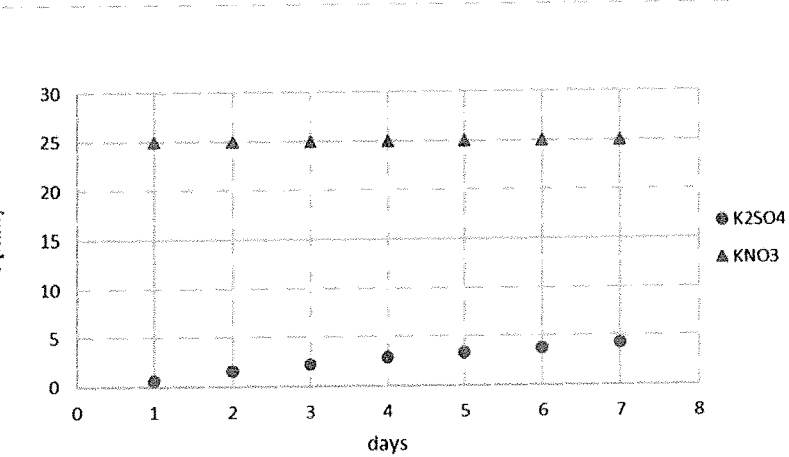
Figure 15:
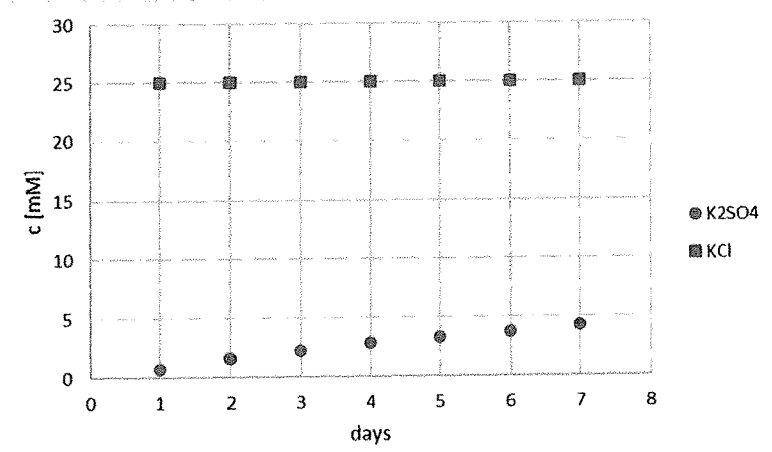

FIG. 9 shows a colour effect of the sensory test for the presence of sulfates(VI) in the solid phase, a solution of a chromophore modified analogue of SQP6 receptor in DMSO was used (left), fully covering solid samples: $KNO_3$ powder (centre) and $K_2SO_4$ powder (right);

FIG. 10 shows a colour effect of a sensory test for the presence of sulfates(VI) in an aqueous solution, a solution of a chromophore modified analogue of SQP6 receptor in nitrobenzene was used (lower phase), and combined with aqueous solutions (upper phase), from the left: clean water, $KNO_3$ solution, $K_2SO_4$ solution;

FIG. 11 shows a view of the crystal structure of receptor SQP6 ($R^1$=$R^2$=$R^3$=$R^4$=$R^5$=F) according to the invention;

FIG. 12 shows a schematic diagram of a U-tube type vessel used for the ion transport experiment through a liquid membrane;

FIG. 13 shows a record of the change of $K_2SO_4$ concentration in the receiving layer as a function of time in the experiment described in Example 9;

FIG. 14 shows s record of the change of $K_2SO_4$ and $KNO_3$ concentration in the receiving layer as a function of time in the experiment described in Example 10;

FIG. 15 shows a record of the change in concentration of $K_2SO_4$ and KCl in the receiving layer as a function of time in the experiment described in Example 11;

DETAILED DESCRIPTION OF THE INVENTION

The invention concerns a receptor of an ion pair for simultaneous removal of oxoanions and their inorganic counterions from aqueous phase, as well as a method of removing oxoanions in the form of inorganic salts from aqueous phase, a sensor for detecting oxoanions, a preparation for removing oxoanions from aqueous solutions and a process of utilisation of aqueous solutions by vitrification.

A Receptor for the simultaneous removal of oxoanions and their counterions from aqueous phase according to the invention contains domains binding oxoanions and domains binding their counterions, wherein the complex formed after the binding of oxoanions and cations remains soluble in a wide range of concentrations in aqueous solutions or organic solutions, which makes possible to carry out an extraction process to another water-immiscible liquid phase and, thus, effectively remove oxoanions from the aqueous phase.

An oxoanion binding domain is a squaramide unit that coordinates oxoanions through amide groups, where hydrogen bonds are formed between amide groups and oxoanionic oxygen atoms, similarly as in proteins binding sulfate(VI)

anions, and in other known oxoanion binding receptors. The general structure of the receptor according to the invention is presented below:

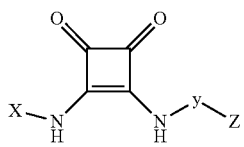

with Z being a crown ether moiety, preferably a benzocrown group, X is any aromatic or aliphatic substituent preferably having functional groups that increase the acidity of squaramide, including Y—Z, and Y is any aliphatic or aromatic substituent preferably having groups capable of forming a hydrogen bond e.g. amide, thioamide, urea, thiourea or ester or Ø (i.e. a direct bond between N and Z).

The binding force of oxoanions by amide groups of squaramide is further increased by substituting it with substituents that increase the acidity of its amide protons, in comparison to unsubstituted squaramide. In general, these substituents reduce electron density in squaramide moiety, which results in an increase of acidity of protons in the amide groups. Therefore, the receptor according to the invention, in contrast to the known solutions, can work in acidic, neutral and slightly alkaline solutions, which is results in the lack of the need of prior stabilisation solutions' pH and simplifies the entire technological process.

Substituents that increase the acidity of amide groups can be freely designed. An example of a squaramide substituent is an aromatic ring with substituents that reduce its electron density, preferably with substituents such as: —F, —$CF_3$ or —$NO_2$. This substituent may also contain an aromatic ring with positively charged substituents, preferably with substituents such as: —$N^+$(Alkyl)$_3$ or —$N^+$(Phenyl)$_3$.

It is also possible to use receptors with substitutes that do not affect or reduce the acidity of the squaramide protons. Then it will be possible to use them in contact with alkaline solutions.

Tris(2-aminoethyl)amine can also be a substituent of squaramide. Tris(2-aminoethyl)amine can be used as a standard substituent or in a special case as a linker between two or three squaramide units linked further to counterion binding domain. In this particular case, a di- or tripodal receptor is formed.

The counterion binding domain is a crown ether of a size suitably selected according to the type of cation bound, being a part of at least one of the aforementioned squaramide substituents. Crown ether is connected to squaramide directly (Y=Ø) or through an aromatic ring, for example, to form a so-called benzocrown group. Moreover, a group containing crown ether can be connected to squaramide through an additional alkyl chain, preferably having groups capable of forming hydrogen bonds, e.g. amide, thioamide, urea, thiourea. Each additional substituent containing amide groups increases the receptor's ability to bind oxoanions.

Crown ether is selected in dedication to the ion pair extracted. According to the invention, one can use i.a. 12-crown-4 ether, 15-crown-5 ether, 18-crown-6, 21-crown-7, or their equivalents containing heteroatoms, preferably with or without additional substituents. According to the invention, crown or benzocrown ether can be a part of one or both substituents of squaramide.

Crown ether moiety as such, when attached to amide group of a squaramide, does not affect the acidity of the protons of the amide group. However, the strength of this interaction increases significantly after binding a cation by crown ether. Due to this effect, simultaneous binding of cations by the same receptor molecule increases its binding force regarding oxoanion. This mechanism has not been used in known ion pair receptors binding oxoanions, including sulfate(VI) anions. It has been observed here, that potassium sulfate(VI) forms with the receptor a complex soluble in organic phase, presumably similar to the one presented in the crystalline structure, i.e. in 4:1 stoichiometry, while monovalent anions probably form a complex in 1:1 stoichiometry, which usually are not soluble. It is possible to create a receptor having more than one moiety containing a crown ether.

The benzocrown moiety can be connected to squaramide via an additional linker, preferably having amide, thioamide, urea, thiourea, ester groups. Preferably, the linker between the squaramide and the benzocrown grouping contains moieties capable of coordinating oxoanions, thereby increasing the binding force in the receptor complex.

According to the invention, the receptors can bind monovalent oxoanions [e.g. nitrites(III) or nitrates(V), rhenates(VII), technetate(VIII)], divalent oxoanions [e.g. sulfite(IV), sulfate(VI)] or trivalent oxoanions [e.g. phosphate(V)]. Counterions are inorganic cations, preferably metal cations of group 1 and group 2 of the periodic table, and radioactive cations, or cations of lanthanides and actinides [e.g. $Li^+$, $Na^+$, $K^+$, $Cs^+$], ammonium cations [e.g. $NH_4^+$, $N^+$(Alkyl)$_4$, $N^+$(Phenyl)$_4$ or tetraphenylborate cations.

When oxoanions and their counterions are bound by a dedicated receptor, a complex is being formed which is soluble in water or organic phase in a wide range of concentrations and which may undergo an extraction process, removing the oxoanion and its counterion from the original solution.

It should be noted that not every receptor will operate with equal efficiency with respect to a specific ion pair: oxoanion-counterion. Determining optimal extraction conditions and optimal receptor structure requires experimental testing in each case. For example, sulfates(VI) in the presence of potassium cations as counterions are removed from aqueous solutions in an efficient manner, especially when using SQP6 receptor dissolved in $CHCl_3$ ($R^2$=$R^4$=$CF_3$; $R^1$=$R^3$=$R^5$=H) with the following structure:

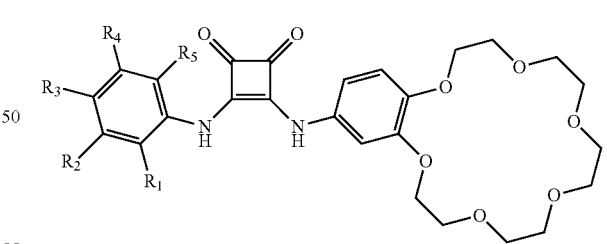

or its derivatives, where $R^1$, $R^2$, $R^3$, $R^4$ and $R^5$ mean hydrogen, or the same or different substitutes that reduce electron density of aromatic ring, preferably —F, —$CF_3$ or —$NO_2$. For example, SQP6 receptor with —$CF_3$ substitutes in positions $R^2$ and $R^4$, and with hydrogen atoms in positions $R^1$, $R^3$ and $R^5$ allows for effective extraction of potassium sulfate(VI) to chloroform solution.

The analogous SQP5 receptor, having 15-crown-5 ether moiety, does not allow extraction nether of sodium sulfate (VI) nor potassium sulfate(VI), because the complex precipitates instead of forming a soluble complex.

Figure 1:
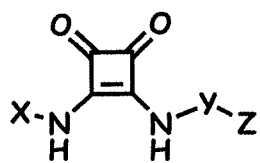
FIG. 1 shows is a schematic structure of the receptor according to the invention, domain for binding oxoanions and domain for binding their counterions, wherein Z is a crown ether moiety, preferably a benzocrown group, X is any substituent, including Y—Z, and Y is any substituent or Ø (i.e. a direct bond between N and Z)
Figure 2:
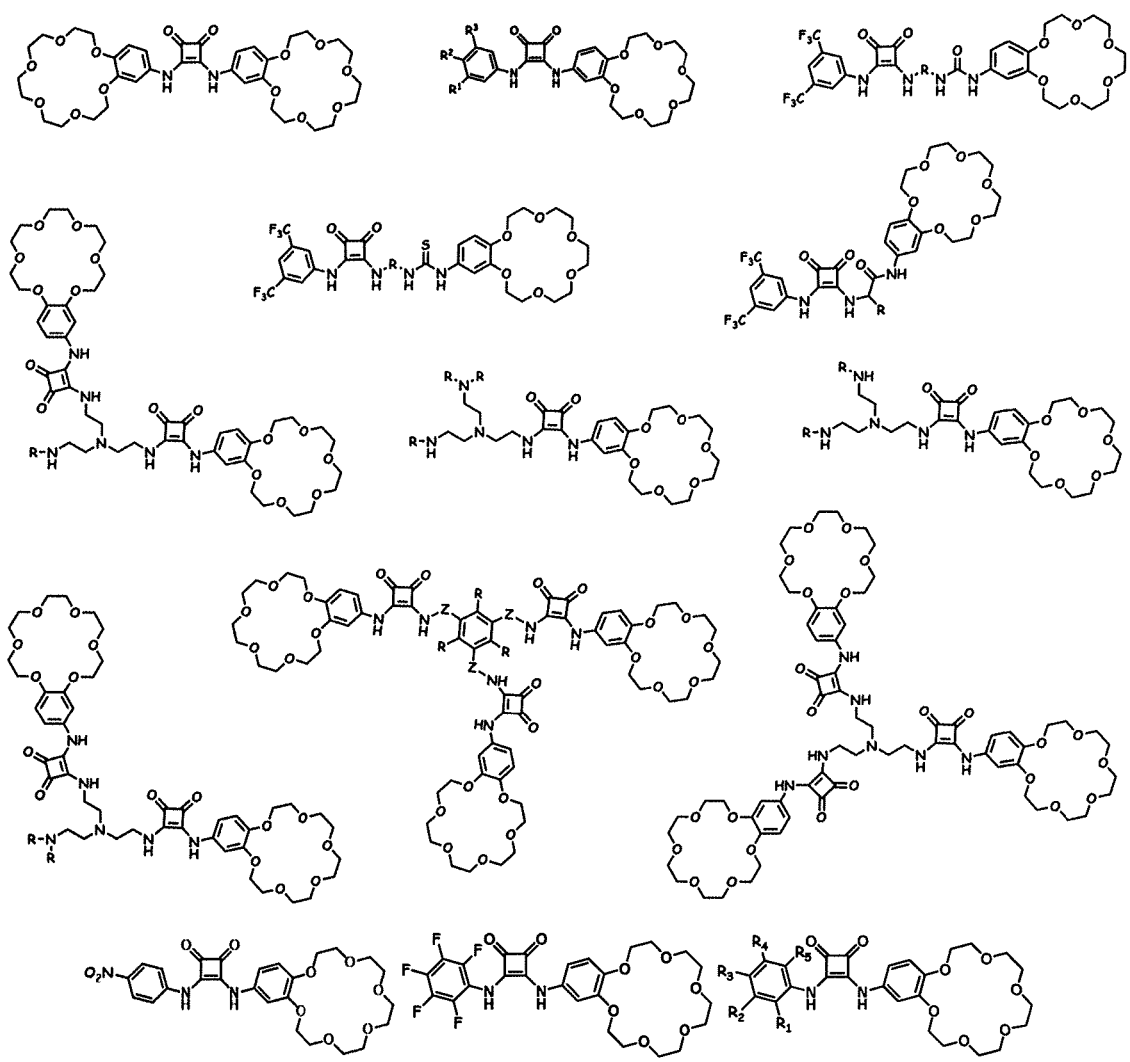
FIG. 2 shows examples of the molecular structures of the receptors according to the invention.
Figure 3:
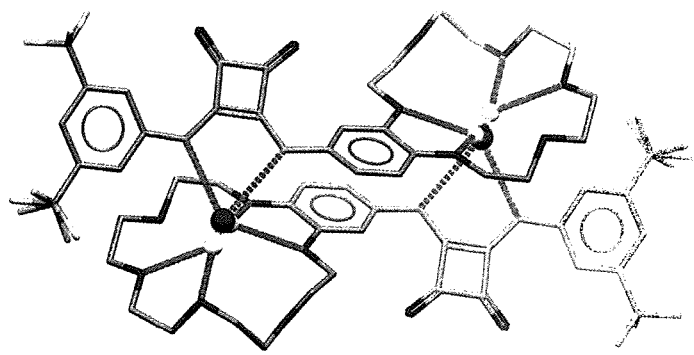
FIG. 3 show a view of the crystal structure of receptor SQP6 ($R^2$=$R^4$=$CF_3$; $R^1$=$R^3$=$R^5$=H) according to the invention.
Figure 4:
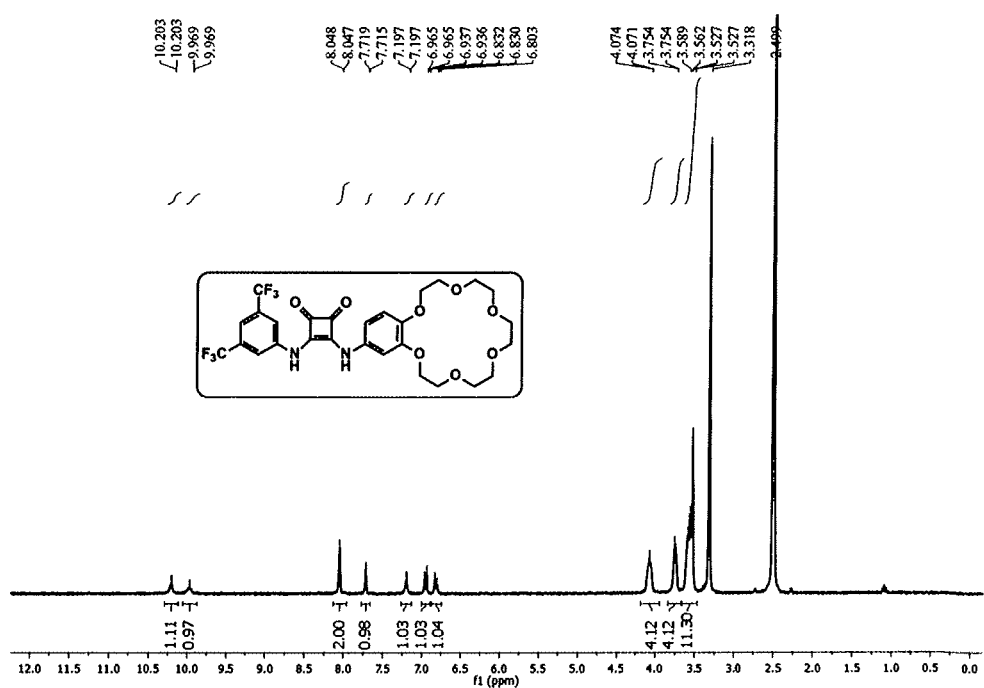
FIG. 4 shows NMR spectrum of SQP6 receptor according to the invention.
Figure 5:
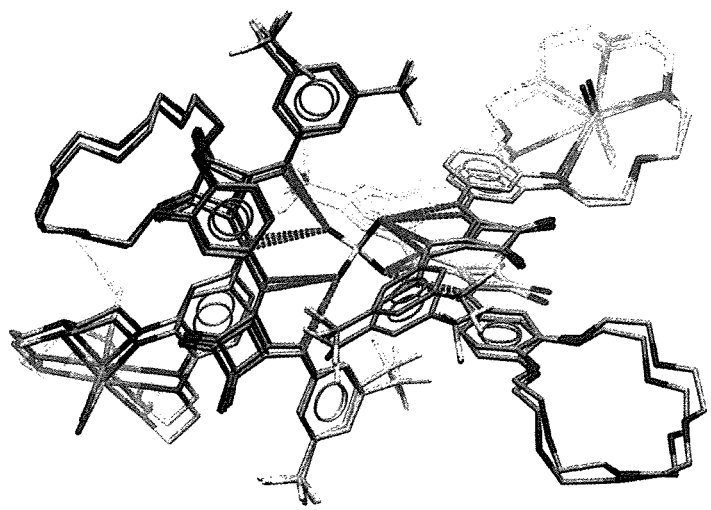
FIG. 5 shows a view of the crystal structure of a complex of receptor SQP6 ($R^2$=$R^4$=$CF_3$; $R^1$=$R^3$=$R^5$=H) according to the invention, binding $Na_2SO_4$, forming a crystalline precipitate.

The complex of SQP6 and sodium sulfate(VI), in the crystal structure, contains four receptor molecules per stoichiometric unit $Na_2SO_4$. The sulfate(VI) anion is coordinated through hydrogen bonds between eight protons of squaramide, while sodium cations occupy two out of four cavities of benzocrown ethers of this complex. The complex has no charge. The visualisation of the molecular structure of this complex is shown in FIG. 5. The complex of SQP6 receptor and sodium sulfate(VI) dissolves in some organic solvents (e.g. chloroform) in a very small scale, which impedes efficient extraction of sodium sulfate(VI) from aqueous phase. However, it is not known, whether an optimisation of extraction conditions and an appropriate choice of a solvent can allow extraction of sodium sulfate (VI) from the aqueous phase using this receptor.

The extraction ability of the ion pair receptors according to the invention presumably rely on design of the receptor's geometry in such way that the complex formed after binding of the ion pair to the receptor does not crystallise easily, thus, it does not form a precipitate but formings clear solutions. This hypothesis is confirmed by the fact that SQP6 receptor complex with potassium sulfate(VI) could not be crystallised even when using conditions analogous to the crystallization of the complex of SQP6 with sodium sulfate(VI). Furthermore, a complex of a analogous SQP5 receptor (having 15-crown-5 ether) precipitates upon extraction, and its crystals can be easily obtained. It is possible that this is the result of a steric hindrance of the molecules forming the complex, which prevents their close packing and crystallisation.

It is possible to design a receptor enabling efficient and selective removal of any oxoanions and their counterions from aqueous phase. This gives an opportunity, after conducting proper tests and experiments, to optimise currently known processes of purification of aqueous solutions from various inorganic oxoanions which negatively affect industrial processes, e.g. removal of sulfates(VI) from radioactive waste before the stage of their utilisation by vitrification, or removal of sulfates(VI) and phosphates(V) during water purification.

A method of removing oxoanions in the form of inorganic salts from aqueous phase according to the invention uses the ion pair receptors described above. For removal of oxoanions from acid solutions, receptors with substituents that increase the acidity of squaramide protons are used, and in the case of an unfavourable effect of receptor deprotonation, receptors with substituents that reduce the acidity of square acid protons can be used.

It is possible to remove oxoanions and their counterions from aqueous phase to another liquid phase by extraction. A water-immiscible solvent, for example an organic solvent, a mixture of organic solvents or an ionic liquid is used for this purpose. It is possible to use such solvents as, e.g. chloroform, nitrobenzene, toluene, ethyl acetate. Extraction of a specific oxoanion with use of a specific receptor requires prior optimisation process and appropriate solvent selection. The solvent must be selected in a way that the ion pair receptor complex is well soluble in it, otherwise the extraction will not be efficient.

Oxoanions and their counterions are removed from aqueous phase into organic phase by extraction with a properly designed preparation (extractant) containing, i.a. the receptor dissolved or dispersed in a properly selected solvent or mixture of solvents. At the moment of contact of the aqueous phase with the organic phase, a complex of the receptor with the ion pair is formed at the interface between these phases, followed by its transfer to the extractant phase. Driving force of this process is the affinity of the complex towards the non-aqueous phase, as well as its low initial concentration in this phase. Alternatively, the receptor is dissolved or suspended in the aqueous phase, where an ion pair receptor complex is formed which then undergo a transfer to the organic phase during extraction. Regeneration of the receptor is possible by consecutive extraction of oxoanions and their counterions back to an excess water phase. The regeneration extraction is carried out with water without said ions, preferably pure water, most preferably with distilled water or deionised water.

It is also possible to remove oxoanions and their counterions from aqueous phase to solid phase by exposing the solution being purified to a suitable adsorbent. A solid adsorbent, modified with receptor molecules or its individual functional groups, removes oxoanions and their counterions from the aqueous phase. The solid phase may form a substrate with an immobilised receptor through which the purified solution being is passed. Alternatively, the solid phase may be a mobile carrier with an immobilised receptor, preferably in the form of a polymer, cross-linked polymer, gel, nanoparticles, magnetic nanoparticles, porous materials. The mobile carrier is mixed with an aqueous solution subjected to purification, and then separated. Regeneration of the solid adsorbent is possible by washing it with an excess water, which allows oxoanions and their counterions migrate back to water phase. For washing, water without said ions, preferably pure water, most preferably distilled water or deionised water is used.

It is also possible to remove oxoanions and their counterions from aqueous phase to another aqueous or organic phase by using a membrane with immobilised, dissolved or suspended receptor or functional groups of this receptor, which membrane separating these phases. Oxoanions and their counterions are bound to the immobilised receptor molecules in the solid or liquid phase of the membrane. Then, bound oxoanions and their counterions migrate through the membrane to the second solution, where the concentration of these ions is smaller, and then dissolve in it. During the process, a stationary state is formed in which a constant migration of oxoanions and their counterions through the membrane towards the solution with a lower concentration occurs. To increase the efficiency of the process, circulation of the receiving solution is done to maintain a constant, low concentration of migrating ions in the receiving solution.

The method of removing oxoanions and their counterions from aqueous phase, according to the invention, allows the process to be carried out over a wide pH range, including acidic solutions. Proper selection of the receptor and the solvent, allows for removal of oxoanions and their counterions from solutions of significantly high concentration, exceeding 2 mM, without the risk of forming a precipitation at the interface.

For the removal of sulfate(VI) anions from aqueous solutions, SQP6 receptor or its derivatives are used, however, the process takes place in the presence of potassium cations as counterions in at least stoichiometric amount relative to sulfate(VI) anions. Preferably, chloroform, nitrobenzene, toluene, or ethyl acetate are used in the extraction process towards the organic phase.

A sensor for detecting oxoanions allows to perform a qualitative test for the presence of specific oxoanions in tested samples.

A sensory solution containing a specific receptor is being used for this purpose, selectively binding specific oxoanions and their counterions, said receptor being dissolved or suspended in an organic solvent or a mixture of organic solvents. The sensory solution changes colour upon contact with a sample containing proper oxoanions, because the resulting complex has a different electronic structure compared to the free receptor. The sensory solution can be used to detect oxoanions in aqueous solutions or in solids. The sensory solution may contain already coordinated counterions, selected in a way that the colour effect is most pronounced, and lipophilic anions such as perchlorates, hexafluorophosphates, tetrafluoroborates facilitating receptor solubiliasation and ensuring charge neutrality of the complex solution.

Alternatively, the sensor may be in a solid form. Then a dedicated receptor or its functional groups are immobilised on a heterogeneous substrate. The solid-state sensor, exposed to a solution containing proper oxoanions, changes colour or other physicochemical parameters, depending on the construction adapted.

Regeneration of sensory solutions and solid-state sensors considers their exposure to an excess of water, preferably deionised or distilled water.

A preparation for removing oxoanions from aqueous phase contains the receptor described above, dissolved or suspended in water-immiscible phase, and a proper amount of counterion to support extraction. The composition of the preparation, i.e. the type of receptor, the type of solvent and the type of counterion, are selected according to specific oxoanions being extracted. A water-immiscible solvent is used, for example an organic solvent, a mixture of organic solvents or an ionic liquid. It is possible to use such solvents as e.g. chloroform, nitrobenzene, toluene, ethyl acetate.

Selection of a suitable counterion supporting extraction is preferable because it helps to avoid the dependence of oxoanion extraction efficiency on an ionic composition of purified solutions. The content of counterions should be at least stoichiometric in relation to the expected complex. The addition of counterions to the receptor solution in an organic solvent also requires the use of anions that neutralise an electric charge of counterions. Anions with lipophilic character are used herein, which do not deactivate the receptor, preferably perchlorates, hexafluorophosphates, tetrafluoroborates.

The preparation for removing sulfate(VI) anions contains SQP6 receptor described above or its derivatives, as well as potassium cations in at least twice lower concentration, and neutraliseing lipophilic anions, preferably perchlorates, hexafluorophosphates, tetrafluoroborates. In this case, chloroform and its solutions are used as the solvent.

A process of vitrification of aqueous solutions, especially those containing radioactive waste, is characterized in that the vitrification step is preceded by the step of removing oxoanions, preferably sulfate(VI) anions, by the method described above, using the receptors described above, preferably using the preparation described above.

A receptor for removing oxoanions from the aqueous phase, a method of removing oxoanions as inorganic salts from the aqueous phase, and a sensor for detecting oxoanions are described in detail in the examples below.

Example 1. A number of receptors were obtained with the molecular structure described in the essence of the invention, which was confirmed by $^1$H NMR measurements.

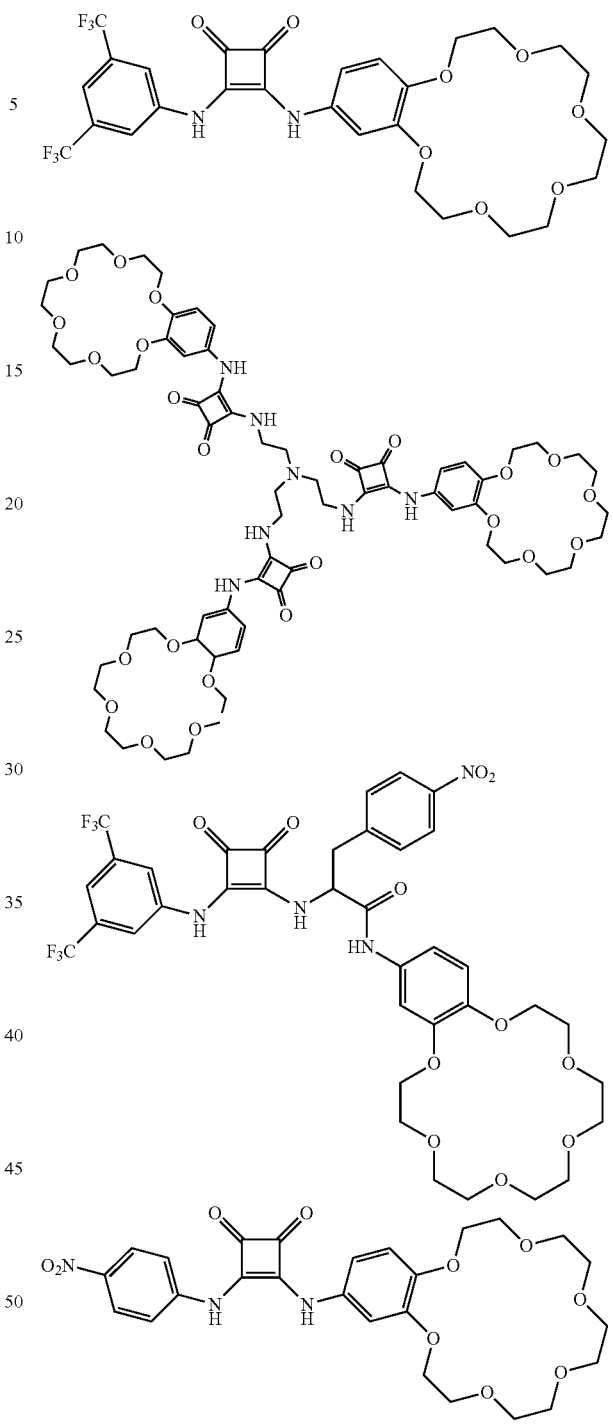

SQP6: $^1$H NMR (300 MHz, DMSO-d$_6$) δ 10.20 (s, 1H), 9.97 (s, 1H), 8.05 (s, 2H), 7.71 (s, 1H), 7.21 (s, 1H), 7.00-6.91 (m, 1H), 6.85-6.77 (m, 1H), 4.15-4.00 (m, 4H), 3.80-3.70 (m, 4H), 3.65-3.42 (m, 12H).

TSQP6: $^1$H NMR (300 MHz, DMSO-d$_6$) δ 9.64 (bs, 1H), 7.53 (bs, 1H), 7.22 (bs, 1H), 7.00-6.67 (m, 2H), 4.20-3.95 (m, 4H), 3.85-3.45 (m, 18H), 2.90-2.70 (m, 2H)

NTSQP6: $^1$H NMR (300 MHz, DMSO-d$_6$) δ10.63 (s, 1H), 10.43 (s, 1H), 8.47-8.35 (m, 1H), 8.23-8.12 (m, 2H), 8.08 (s, 2H), 7.68 (s, 1H), 7.57-7.45 (m, 2H), 7.25-7.16 (m,

1H), 7.14-7.07 (m, 1H), 6.98-6.90 (m, 1H), 5.25-5.10 (m, 1H), 4.10-4.00 (m, 4H), 3.83-3.70 (m, 4H), 3.65-3.50 (m, 12H), 3.43-3.17 (m, 2H)

NO2SQP6: $^1$H NMR (300 MHz, DMSO-d$_6$) δ 10.28 (s, 1H), 9.97 (s, 1H), 8.34-8.22 (m, 2H), 7.71-7.61 (m, 2H), 7.23 (s, 1H), 7.03-6.78 (m, 2H), 4.20-3.95 (m, 4H), 3.88-3.69 (m, 4H), 3.69-3.38 (m, 12H).

Example 2. Extraction of potassium salts using the SQP6 receptor. Extraction of aqueous solutions of KCl, KBr, KNO$_3$, KNO$_2$ and K$_2$SO$_4$ salts at 50 mM (1 ml) with a 2 mM solution of SQP6 receptor in deuterated chloroform (1 ml) was performed. Only in the case of extraction of the aqueous K$_2$SO$_4$ solution, separation of homogeneous phases (aqueous and organic) was observed. In the case of attempts to extract the remaining salts, precipitation of the formed complex was observed in individual phases or at the interface. An attempt was also made to transfer K$_2$SO$_4$ back to the aqueous phase by washing the chloroform solution in which the complex is formed with a large portion of deionized water. A reference experiment was also carried out involving the extraction of an aqueous K$_2$SO$_4$ solution with pure chloroform.

Organic samples were subjected to $^1$H NMR analysis. The results of the analysis are shown in FIG. 7: a) spectrum of receptor solution in deuterated chloroform after contact with water; b) spectrum of the receptor solution in deuterated chloroform after contact with K$_2$SO$_4$ water solution; c) spectrum of receptor solution in deuterated chloroform after washing with water again. Comparison of the obtained spectra indicated presence of the complex of receptor and potassium sulfate(VI) in the organic phase in sample b). This was confirmed by the change of chemical shifts of sq uaramide protons signals, which are higher after formation of the complex than in a free receptor.

The presence of potassium in the organic layer was confirmed by atomic emission spectroscopy. The samples obtained after extraction of the K$_2$SO$_4$ aqueous solution 50 mM (1 ml) with 2 mM solution of SQP6 receptor in chloroform (1 ml) and with pure chloroform (1 ml) were compared. After phase separation, 0.5 ml of the organic layer was taken from each sample and diluted to 5 ml with a polar solvent miscible with chloroform. AES analysis was carried out confirming the ability of the receptor to extract of potassium sulfate from the aqueous layer to the organic layer. This is evidenced by the content of potassium ions in the organic layer containing the SQP6 receptor and the lack of potassium content in the organic phase lacking the receptor. The content of potassium (refers to the receptor) in the organic phase containing SQP6 was found to be 36% what correspond to 72% yield of potassium sulfate extraction (4:1 complex formation Assumed)

Example 3. Extraction of potassium nitrate using the SQP6 receptor. Extraction of an aqueous solution of 50 mM KNO$_3$ (1 ml) was performed with a 2 mM receptor (SQP6) solution in chloroform (1 ml). After phase separation, 0.5 ml of the organic layer was taken from the sample and diluted to 5 ml with a polar solvent miscible with chloroform. AES analysis was performed to confirm the content of potassium ions in the organic layer. Based on this, 1.2% potassium receptor loading was calculated. It is noteworthy that with prolonged exposure of aqueous and organic solutions, a precipitate appears at the interface.

Example 4. Extraction from a mixture of potassium nitrate(V) and potassium sulfate(VI) using the SQP6 receptor. Extraction of 2 ml of an aqueous solution containing a mixture of K$_2$SO$_4$ and KNO$_3$ (5 mM each salt) in water was performed with a 2 ml solution of the SQP6 receptor in chloroform. Extraction was carried out in two variants, using solutions with a concentration of 5 mM and 20 mM receptor in chloroform. After phase separation, 1 ml of the aqueous layer was taken, diluted to 10 ml with deionized water and subjected to chromatographic analysis. For comparative purposes, 1 ml of an initial aqueous solution containing a mixture of K$_2$SO$_4$ and KNO$_3$ diluted to 10 ml with deionized water was also subjected to chromatographic analysis. The results of the analyses are shown in FIG. 8: a) the mother liquor after a 10-fold dilution; b) an aqueous solution of the salt mixture after extraction with chloroform solution of 5 mM SQP6 receptor-10-fold dilution; c) aqueous solution of the salt mixture after extraction with a 20 mM SQP6 receptor chloroform solution—10-fold dilution. It was observed that extraction with a 5 mM SQP6 receptor solution resulted in a decrease in the concentration of potassium nitrate by 4.9% and potassium sulfate by 25%. Next, after extraction with 20 mM SQP6 receptor solution, a decrease in the concentration of potassium nitrate salt by 7.2% and potassium sulfate(VI) by 74% was observed. The obtained result indicates the selectivity of the SQP6 receptor for potassium sulfate over potassium nitrate.

Example 5. Extraction of sodium sulfate using SQP5 receptor, failed at concentrations above 1 mM. Extraction of an aqueous solution of Na$_2$SO$_4$ and K$_2$SO$_4$ at a concentration of 50 mM (1 ml) with a 2 mM receptor solution (SQP5) in chloroform (1 ml) was performed. In no case was complete phase separation recorded. However, the appearance of precipitate was observed. The structure of the SQP5 receptor used ($R^2$=$R^4$=$CF_3$; $R^1$=$R^3$=$R^5$=H) is illustrated by the following structural formula:

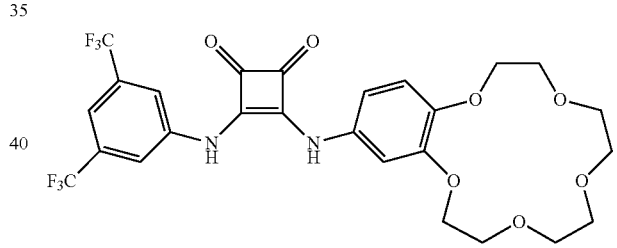

Example 6. Action of sensory solutions for testing solids. A yellow-orange sensory solution contains 2.1 mM SQP6 ($R^3$=$NO_2$; $R^1$=$R^2$=$R^4$=$R^5$=H) receptor solution in DMSO. KNO$_3$ and K$_2$SO$_4$ crystals were placed in separate vials were covered with sensory solution. A third vial without solid samples was prepared as a reference experiment and contained only sensory solution. The sensory solution turned purple only when in contact with solid K$_2$SO$_4$, while in the remaining vials the colour remained unchanged. The results are shown in FIG. 9.

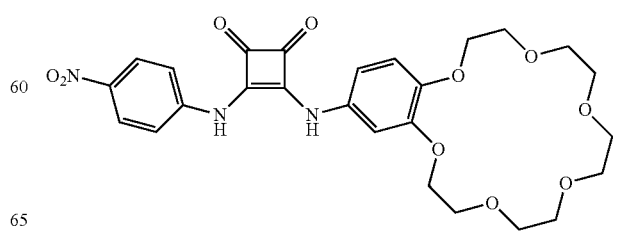

Example 7. Action of sensory solutions for testing aqueous solutions. A yellow sensory solution contains 0.5 mM SQP6 receptor derivative ($R^3$=$NO_2$; $R^1$=$R^2$=$R^4$=$R^5$=H) in nitrobenzene. Sensory solution was mixed with two aqueous solutions containing: 50 mM $KNO_3$, 50 mM $K_2SO_4$ and deionized water. The sensory solution (organic phase) turned red only when in contact with the $K_2SO_4$ solution, while the colour remained unchanged in the remaining vials. The results are shown in FIG. 10.

Figure 6:
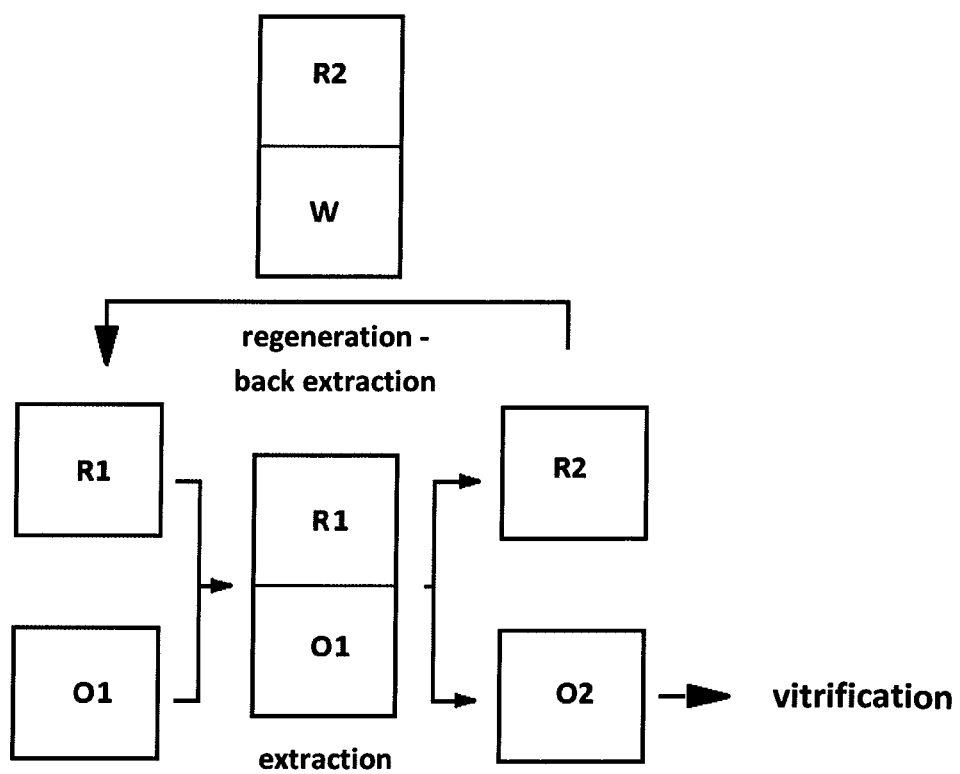
FIG. 6 shows a block diagram of the process of removal of oxoanions and their counterions from aqueous phase using a receptor according to the invention, where.

Example 8. Utilization of radioactive waste by vitrification. The radioactive waste utilization process is carried out in a known manner, with the only difference that the mixture is treated with a receptor before vitrification (as described in either an organic solution or on a carrier) and then after the separation of the receptor, the waste is subjected to a standard procedure. The obtained borosilicate glass, in the absence of excess of sulfates(VI), does not corrode and does not crack, which eliminates the risk of hazardous radioactive leaks. Diagram FIG. 6.

Example 9. Continuous process of potassium sulfate(VI) removal by transport through a bulky liquid membrane using SQP6 receptor. A bulky liquid membrane (8 ml) consists a 5 mM SQP6 receptor solution ($R^1$=$R^2$=$R^3$=$R^4$=$R^5$=F) in chloroform (receptor structure in FIG. 11), deposited on the bottom of a U-tube, separating the primary phase from the receiving phase, which filled subsequent necks of the vessels (diagram in FIG. 12). The source phase was 50 mM $K_2SO_4$ aqueous solution (8 ml), while the receiving phase was distilled water (8 ml). The increase in salt concentration in the receiving phase was monitored for a week using conductometry. An increase of the concentration of $K_2SO_4$ in the receiving phase was observed and was calculated to be ca. 10 mM after 7 days of the experiment (FIG. 13), what correspond to transport ca. 1/5 of $K_2SO_4$ from the primary phase to the receiving phase. The amount of transported $K_2SO_4$ (about 80 µmol) doubled the amount of receptor used (40 µmol), which proves of the lability of the complex formed. The structure of the SQP6 receptor used ($R^1$=$R^2$=$R^3$=$R^4$=$R^5$=F) is illustrated by the following structural formula:

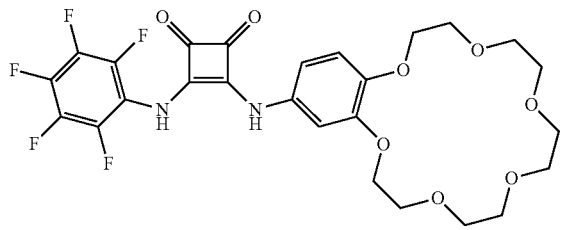 [SMILES: O=c1c(Nc2ccc3c(c2)OCCOCCOCCOCCOCCO3)c(Nc2c(F)c(F)c(F)c(F)c2F)c1=O]

Example 10. Continuous process of potassium sulfate(VI) removal in the presence of potassium nitrate(V) by transport through a bulk liquid membrane using the SQP6 receptor. The experiment was carried out in the system used in Example 9 with the difference that the primary phase (8 ml) consisted an aqueous solution of $K_2SO_4$ (50 mM) and $KNO_3$ (25 mM), and the receiving phase contained 25 mM aqueous solution of $KNO_3$ (8 ml). The selected receiving phase was designed to prevent competitive nitrates(V) transport in the presence of sulfate(VI) salts. The increase in salt concentration in the receiving layer was monitored by ion chromatography for a week. An increase in the concentration of $K_2SO_4$ in the receiving phase was observed to reach a value of ca. 5 mM during 7 days of the experiment (FIG. 14), what corresponds to transport of ca. 1/10 of $K_2SO_4$ from the source phase. Slower $K_2SO_4$ migration compared to example 9 may result from a lower ionic strength gradient between layers and partial complexation of the receptor by $KNO_3$.

Example 11. Continuous process of removing potassium sulfate in the presence of potassium chloride by transport through a bulk liquid membrane using the SQP6 receptor. The experiment was carried out in the system used in Example 10 with the difference that the primary phase (8 ml) contained an aqueous solution of $K_2SO_4$ (50 mM) and KCl (25 mM), and the receiving phase contained 25 mM aqueous KCl solution (8 ml). The selected receiving phase was designed to prevent competitive chloride transport in the presence of sulfate(VI) salts. The increase of salt concentration in the receiving layer was monitored by ion chromatography for a week. An increase in the concentration of $K_2SO_4$ in the receiving phase was observed to reach a value of ca. 5 mM during 7 days of the experiment (FIG. 15), what corresponds to ca. 1/10 of $K_2SO_4$ from the source phase to the receiving layer. Slower $K_2SO_4$ migration compared to example 9 may result from a lower ionic strength gradient between layers and partial complexation of the receptor by KCl, similarly to the case in example 10.

Example 12. Continuous process of potassium sulfate(VI) removal by transport through a solid membrane containing the SQP6 receptor. An experiment was carried out in a system analogous to the system used in Examples 9-11 with the difference that a solid carrier modified with SQP6 units was used as the membrane. The transport of $K_2SO_4$ was noted to be less effective than in Examples 9-11 due to slower diffusion in the solid membrane.

The invention claimed is:

1. A method of removing alkali metal sulfates (VI) from aqueous phase, using receptors in the form of organic molecules containing amide groups specifically coordinating sulfate (VI) anions as well as moieties specifically coordinating alkali metal cations, the receptor(s) having the general formula (I):

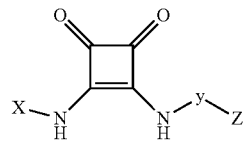

wherein
X is any aliphatic or aromatic group,
Y is a direct bond or a linker selected from any aliphatic or aromatic group,
Z is a crown ether moiety.

2. The method according to claim 1, wherein the alkali metal sulfates (VI) are removed from aqueous phase to organic phase by dissolving or suspending the receptor(s) in a suitably selected organic solvent or in a mixture of organic solvents, followed by extraction of the alkali metal sulfates (VI) from the aqueous phase to this organic phase, whereby the sulfate (VI) anions and their alkali metal counterions are simultaneously bound by the receptor in the form of a soluble complex.

3. The method according to claim 1, wherein the alkali metal sulfates (VI) are removed from aqueous phase to organic phase by dissolving or suspending the receptor(s) in aqueous phase containing the alkali metal sulfates (VI), simultaneous binding of sulfate (VI) anions and their alkali metal counterions by the receptor(s), followed by extraction of the formed complex containing sulfate (VI) anions and their alkali metal counterions to a suitably selected organic solvent or a mixture of organic solvents in the form of a soluble complex.

4. The method according to claim 1, wherein the alkali metal sulfates (VI) are removed from aqueous phase to solid phase by passing the aqueous phase containing the alkali metal sulfates (VI) through a stationary phase containing the receptor immobilized on a heterogenous substrate.

5. The method according to claim 1, wherein the alkali metal sulfates (VI) are removed from aqueous phase to solid phase by means of a homogeneous or heterogeneous medium with the receptor immobilized thereof.

6. The method according to claim 1, wherein the alkali metal sulfates (VI) are removed from one aqueous phase to an immiscible phase that is immiscible with the one aqueous phase by using a membrane for separating the one aqueous phase and the immiscible phase, the membrane being either in a form of a layer of organic solution containing the receptor(s) dissolved in that organic solution or in a solid form with the receptor(s) immobilized thereon.

7. The method according to claim 1, wherein sulfate(VI) anions are removed from aqueous solutions in the presence of at least a stoichiometric amount of potassium cations as counterions, using a receptor of formula (II):

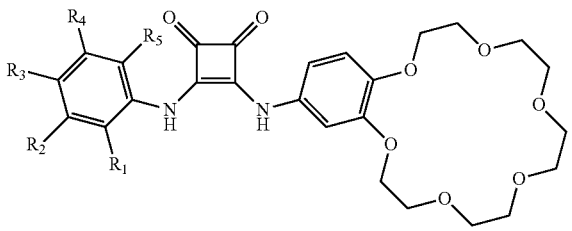

Wherein each of $R_1$, $R_2$, $R_3$, $R_4$ and $R_5$ independently denotes a hydrogen atom, or a substituent reducing electron density of the aromatic ring or derivatives of such a receptor(s).

8. The method according to claim 1, wherein
X comprises functional groups increasing the acidity of squaramide,
Y is a linker substituted by at least one group capable of hydrogen bonds, and
Z is a benzocrown group.

9. The method according to claim 8, wherein X is an aromatic ring substituted by at least one substituent selected from —F, —$CF_3$, —$NO_2$, —$N^+(alkyl)_3$ and —$N^+(phenyl)_3$.

10. The method according to claim 8, wherein Y is a linker substituted by at least one group capable of hydrogen bonds, selected from amide, thioamide, urea, thiourea and ester group.

11. The method according to claim 1, wherein Z is selected from the moieties of the following crown ethers: 12-crown-4-ether, 15-crown-5-ether, 18-crown-6-ether, 21-crown-7-ether.

12. The method according to claim 1, wherein X=—Y—Z.

13. The method according to claim 1, wherein —NH—X group is a tris(2-aminoethyl)amine moiety.

14. The method according to claim 1, wherein the receptor is selected from the following compounds:

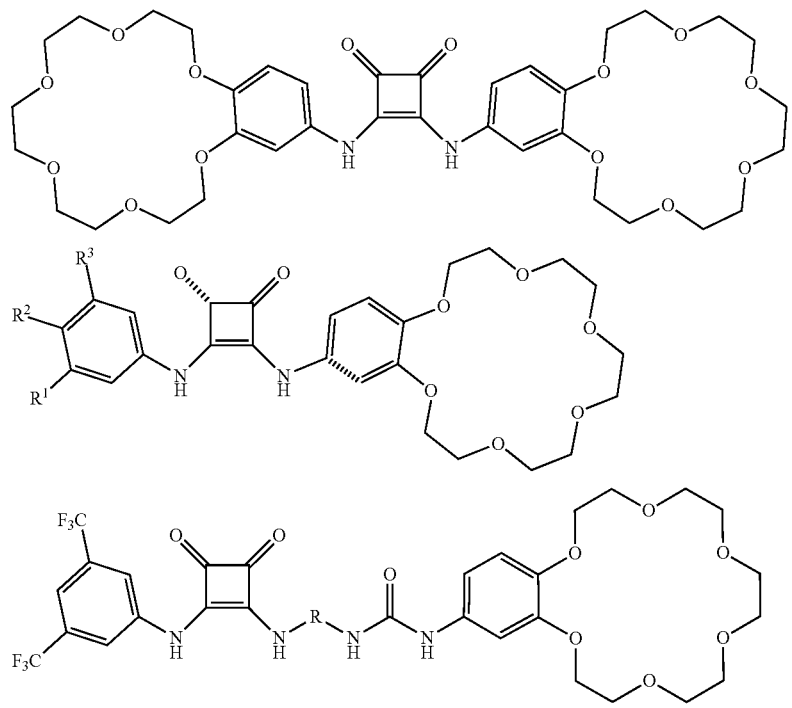

-continued
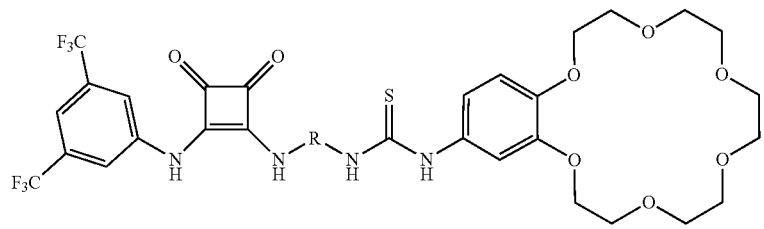
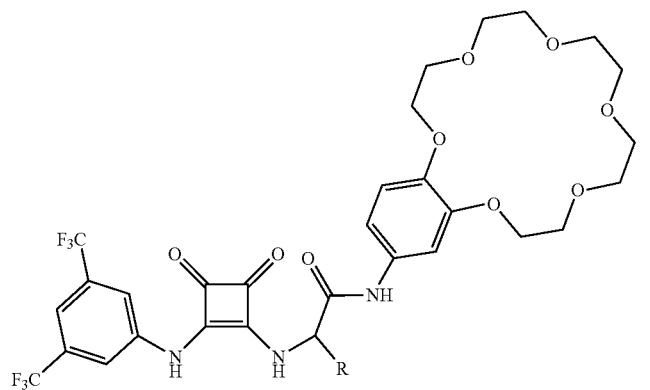
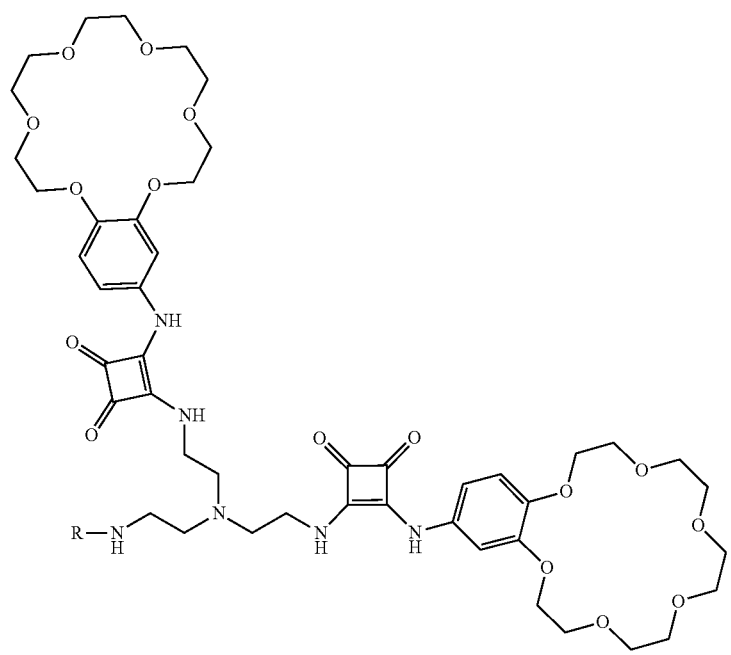
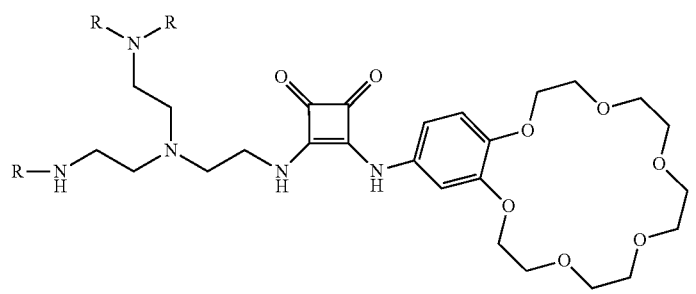

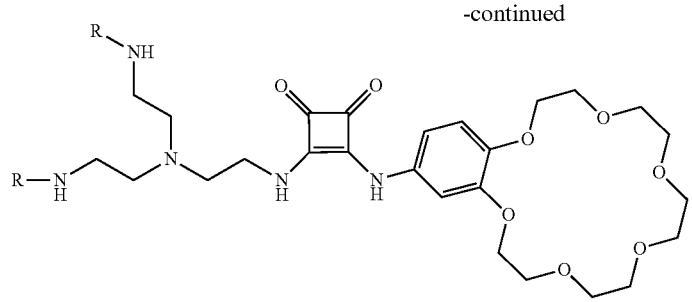
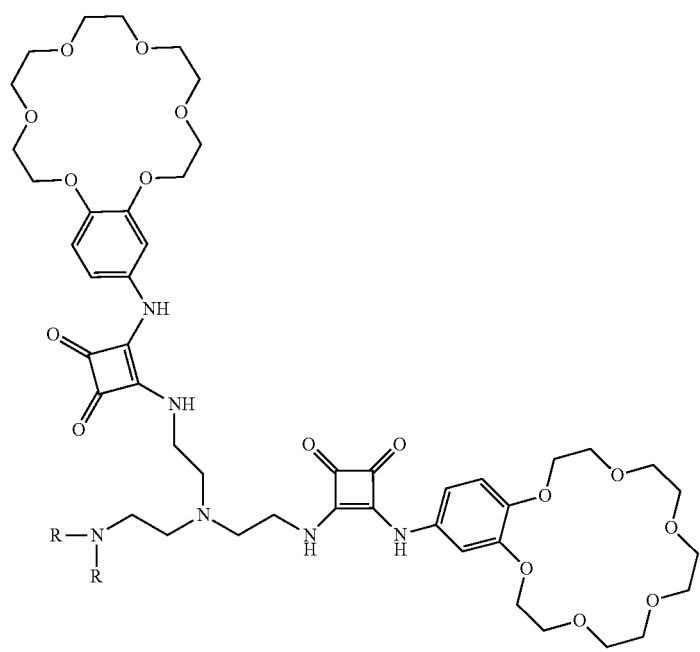
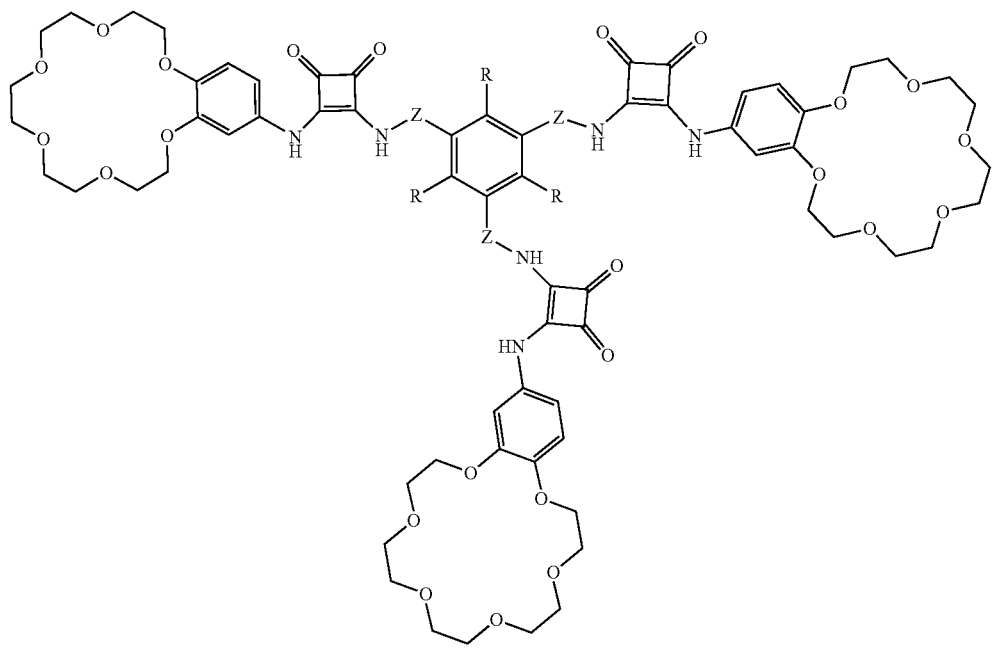

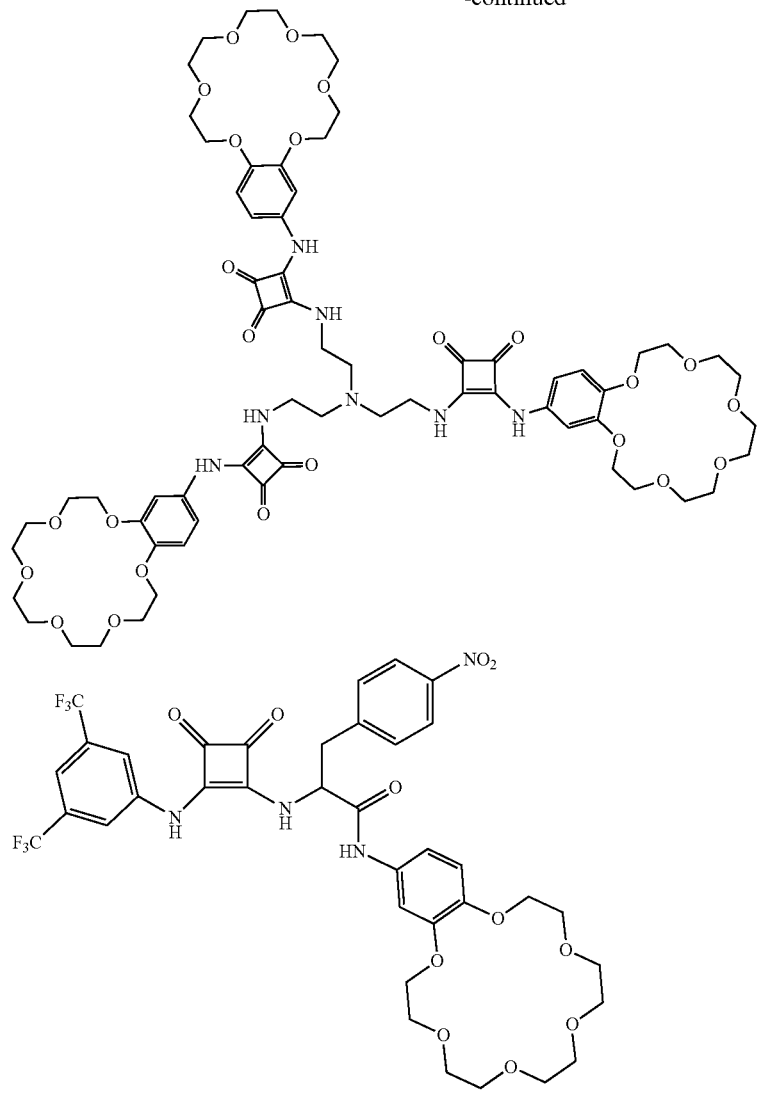

15. The method according to claim 7, wherein in the formula (II) each of $R_1$, $R_2$, $R_3$, $R_4$ and $R_5$ independently denotes a hydrogen atom, —F, —$CF_3$ or —$NO_2$.

16. The method according to claim 8, wherein the receptor is selected from the following compounds:
 a compound of formula (II), wherein $R_2$=$R_4$=—$CF_3$ and $R_1$=$R_3$=$R_5$=H,
 a compound of formula (II), wherein $R_3$=—$NO_2$ and $R_1$=$R_2$=$R_4$=$R_5$=H,
 a compound of formula (II), wherein $R_1$=$R_2$=$R_3$=$R_4$=$R_5$=F.

* * * * *